United States Patent [19]
Mizuno et al.

[11] Patent Number: 5,337,094
[45] Date of Patent: Aug. 9, 1994

[54] EYE OBSERVATION APPARATUS

[75] Inventors: Seinosuke Mizuno; Yoshihiko Yamada, both of Nagoya, Japan

[73] Assignee: Tomey Corporation, Nagoya, Japan

[21] Appl. No.: 834,761

[22] Filed: Feb. 13, 1992

[30]     Foreign Application Priority Data

Feb. 15, 1991 [JP] Japan .............................. 3-006232[U]
Jan. 16, 1992 [JP] Japan ................................... 4-005509

[51] Int. Cl.5 ................................................ A61B 3/14
[52] U.S. Cl. ........................................ 351/206; 351/221; 354/62
[58] Field of Search ....................... 351/221, 210, 206; 359/799; 354/62

[56]        References Cited
U.S. PATENT DOCUMENTS
4,209,225  6/1980  Kumiomi et al. ...................... 350/46

*Primary Examiner*—William L. Sikes
*Assistant Examiner*—Hung Xuan Dang
*Attorney, Agent, or Firm*—Armstrong, Westerman, Hattori, McLeland & Naughton

[57]        ABSTRACT

Eye observation apparatus composed of an illumination optics which is fixed on a frame of a main body and illuminates, a portion of inspection, a photographic optics system for for causing an image ray which is emitted from the portion of inspection to reach an image plane, a photographing means movably equipped in the frame of the main body along with an optical axis and a biasing means for biasing the photographing means so that a tip portion of the photographing means coming into contact with an eye slightly.

3 Claims, 6 Drawing Sheets

EYE OBSERVATION APPARATUS

BACKGROUND OF THE INVENTION

The present invention relates to an eve observation apparatus, and more particularly to an observation apparatus wherein tip portion comes into contact with an eye, observes and photographs each portions of the eye such as vitreous body, retinal vessel cornea, corneal epithelium.

As a conventional eye observation apparatus, the apparatus which is described in Japanese Examined Patent Publication No. 36969/1983 is known.

This observation apparatus as shown in FIG. 6 comprises a lens barrel 52, a main body 54 including an imaging lens unit 55, a photographing section 56 and an illumination optics 57 and a biasing means 58. Object compound lens unit which is stored in the lens barrel 52 is movable to the main body 54 along with the optical axis. The biasing means 58 biases the lens barrel 52 in the direction of an eye so that a tip portion of the objective lens unit is constantly contacted with the eye. Even if the eye which is an object of inspection moves, follow-up movement of the object compound lens unit following the movement of the eye prevents out of focus.

Accordingly, a focusing system is equipped in the object compound lens unit since it is necessary that collimated image ray which is emitted from the object compound lens unit is necessary to reach the image compound lens 55.

Further, the conventional observation apparatus, plurality of covered conductors is connected between the object compound lens unit and the main body as the electrical cable for supplying electric power with the focusing system and the electrical cable for electric signal.

However, when the covered conductors are used, it is difficult that the eye is coming into contact with the tip portion of the object compound lens due to a reaction force which is generated by bending the covered conductors when a movable portion is moved. Then, the coil of bare conductor which has a good flexibility and small diameter has recently been used instead of the covered conductor. That is to say, the covered conductor 63a is connected to a fixed portion ( main body 54 ) via an insulating plate 61a and an insulating substrate 62a.

The covered conductor 63b is connected to the movable portion (object compound lens unit 53) via the insulating plate 61b and the insulating substrate 62b. The covered conductor 63a is soldered to an end portion of the coil 64 and the covered conductor 63b is soldered another end portion of the coil 64 so as to be conducted. One covered conductor 63a is connected to a power source (not shown) and t he other covered conductor 63b is connected to a driving portion (not shown) of the object compound lens unit 53. Plurality of bare wire coil units are used.

The conventional observation apparatus 5 mentioned hereinbefore requires such a troublesome work as to position the optical axis of the movable object compound lens unit 53 and the optical axis of the fixed main body 54. The conventional observation apparatus further requires to collimate the image ray and provide the collimated image ray with the image compound lens unit 55. Therefore, focusing system requires to be equipped in the object compound tens unit 53. Thus, the location of equipping the focusing system is limited.

Main object of the present invention is to delete the above-mentioned problems and to provide an eye observation apparatus of which assembly is very easy since it is no need for positioning the optical axis of the movable portion and the optical axis of the fixed portion. Moreover, the object of the invention is to provide an eye observation apparatus of which focusing system can be selected and/or equipped at will in the object compound lens, the image compound lens or the image plane portion.

SUMMARY OF THE INVENTION

In accordance with the present invention there is provided an eye observation apparatus comprising an illumination optics which is fixed on a frame of a main body, said illuminating optics illuminating a portion of inspection, a photographing optics photographing for causing an image ray which is emitted from said portion of inspection to reach an image plane, a photographing means movably equipped to said frame of the main body along with an optical axis and a biasing means for biasing said photographing means so that a tip portion of said photographing means coming into contact with an eye slightly.

The above-mentioned photographing means preferably has object compound lens and image compound lens having convex compound lens and concave compound lens in such a manner that said convex compound lens located in the side of said object compound lens are alienated from said concave compound lens in the side of said image plane. In the above-mentioned eye observer ion apparatus, either said convex compound lens or said concave compound lens are movable on the optical axis.

It is preferable that said photographing means has an electrical equipment and a flexible electrical cable for electrical connection is equipped between said photographing means and said frame of main body.

As the flexible electrical cable, there is such a flexible electrical cable as to comprise plurality of foils having electric conductivity and a synthetic resin film, said synthetic resin film being onesideally attached to said plurality of foils.

The convex compound lens argued in claims is a concept including a convex lens, combination of plurality of convex lenses and combination of the convex lens and the concave lens which functions totally as a convex lens. The concave compound lens argued in claims is a concept including a concave lens, combination of plurality of the convex lenses and combination of the convex lens and the concave lens functions totally as a concave lens.

According to an eye observation apparatus of the present invention, the apparatus has such a construction that the whole photographing means including a photographic optics, an eyepiece and a camera can be moved on a frame of a body. Therefore, out of focus (displacement of focus ) does not happen due to the follow-up movement of the whole photographing means even if an eye which is an object of inspection moves slightly.

DETAILED DESCRIPTION

Hereinafter, an eye observation apparatus of the present invention is explained with referring to attached drawings.

Figure 1:
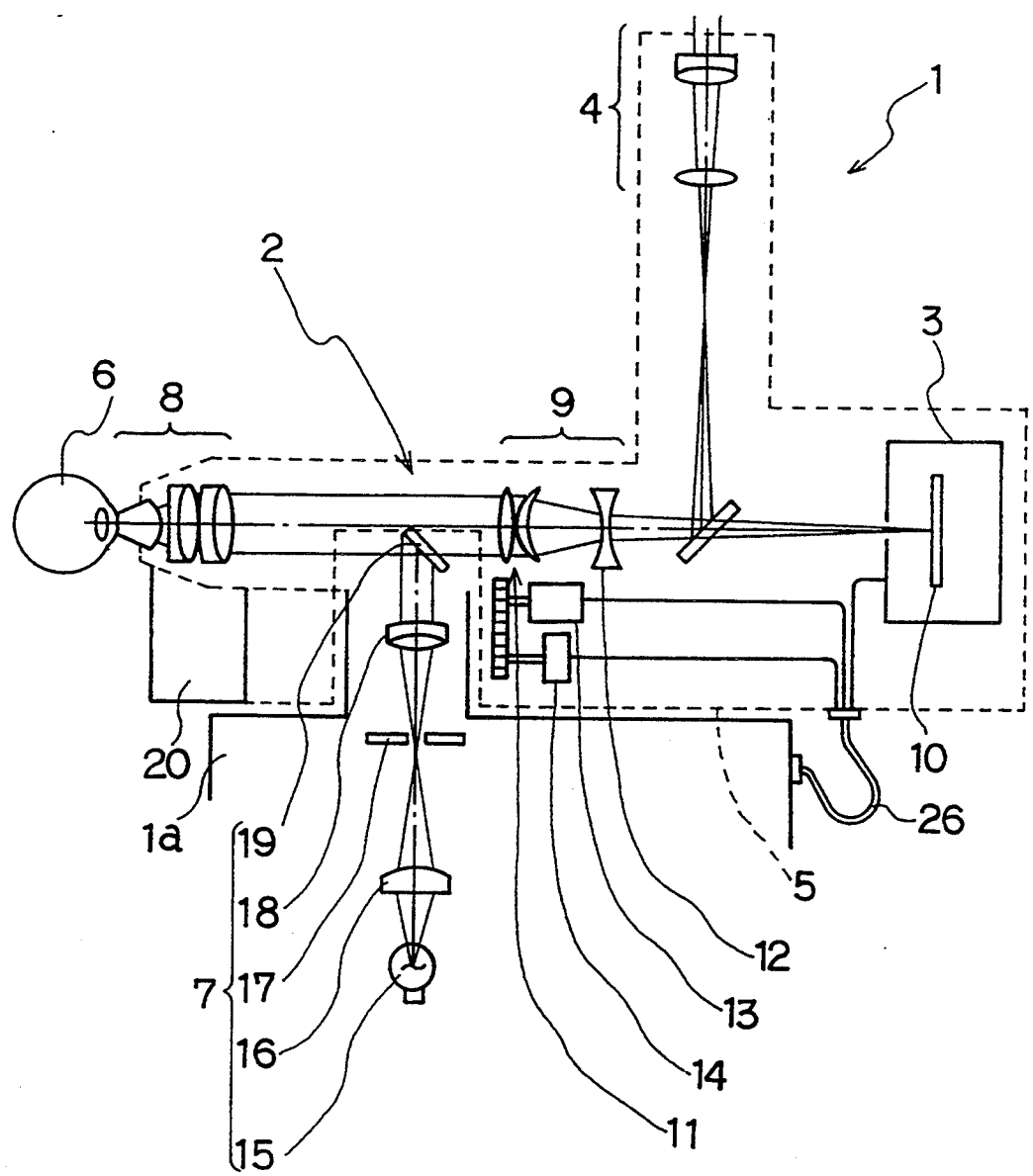
FIG. 1 is an optical-path diagram showing an embodiment of the present invention.

In FIG. 1, numeral 1 denotes the eye observation apparatus (hereinafter referred to as an observation apparatus), whole photographing means 5 including photographic optics 2, a camera 3 and an is eyepiece 4 is movably supported on a frame 1a of a main body. An is an illuminating optics 7 for illuminating an eye which is an object of inspection is fixed to the frame 1a. Since whole photographing means 5 can be moved, positioning an optical axis of movable portion of the object compound lens 8 and the optical axis of a fixed portion of the main body is not required. Therefore, assembling the apparatus is easy.

A moving mechanism of the above-mentioned photographing means 5 has such a construction as normally used that friction due to a movement of the photographing means 5 is reduced as small as possible. For example, said mechanism is sometime composed of a guiding barrel fixed to the frame 1a and inserted by the photographing means 5 and plural steel balls enclosed between the guiding barrel and the photographing means 5.

The photographic optics 2 has an object compound lens 8 and an image compound lens 9 in such a manner that the object compound lens 8 is alienated from the image compound lens 9. The image compound lens 9 has such a function that transmitted image ray through the object compound lens 8 is imaged on an image plane 10 in the above-mentioned camera 3. The image compound lens 9 has such a construction composed of a convex compound lens 11 (located in the side of the object compound lens 8) and a concave compound lens 12 (located in the side of the image plane 10) that the convex compound lens 11 is alienated from the concave compound lens 12. The convex compound lens 11 is provided with a function of focusing by means of a movement thereof on the optical axis.

Figure 2:
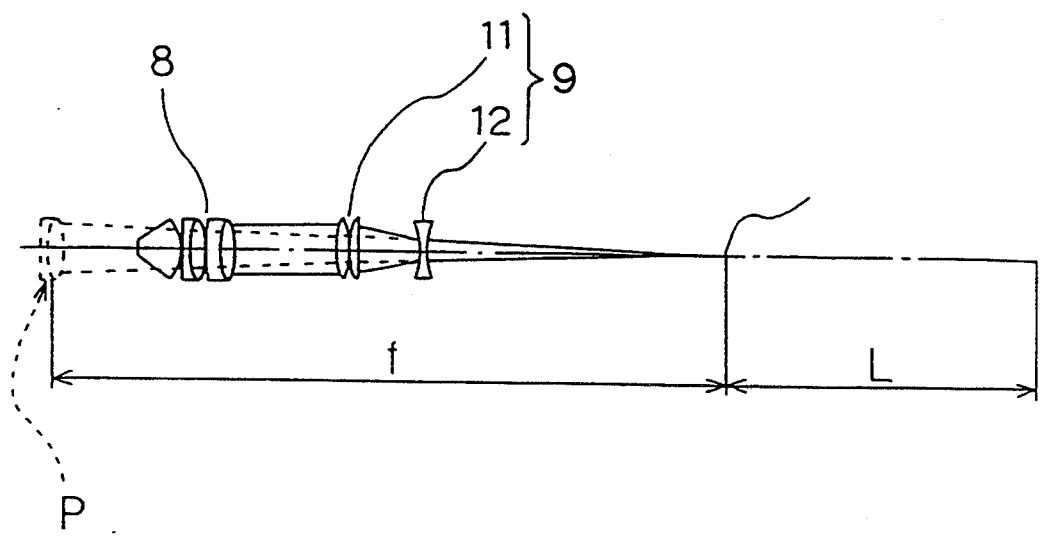
FIG. 2 is an optical-path diagram illustrating focal distance of an image compound lens in an eye observation apparatus of FIG. 1.
Figure 3:
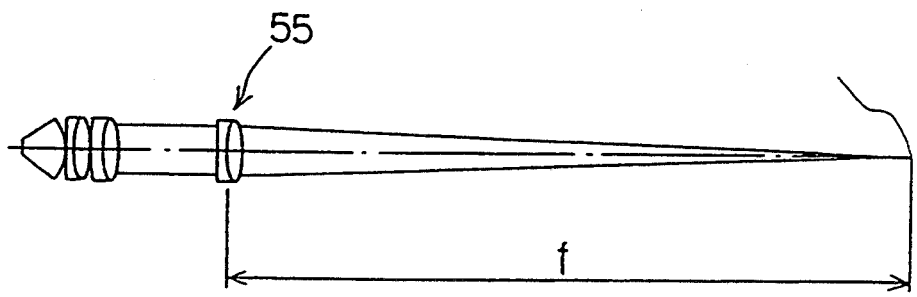
FIG. 3 is an optical path diagram illustrating focal distance of an image compound lens in an example of conventional eye observation apparatus.

When the image compound lens 9 has such a construction that the convex compound lens 11 is alienated from the concave compound lens 12, total length of the apparatus 1 can be short. That is to say, the image ray is converged by the convex compound lens 11 of the image compound lens 9, then the image is ray diverged (i.e. convergent angle is caused to be small) by the concave compound lens 12 so that the image ray is imaged on the image plane 10 as shown in FIG. 2. In this case, if focal length of the image compound lens 9 is set to the same focal length "f" as that of the conventional observation apparatus 51 shown in FIG. 3 (the image compound lens unit 55 is composed of the convex compound lens 55 ), the situation of the observation apparatus 1 is as same situation that the image compound lens unit 55 is located in the position "p". Then, the distance between the image compound lens 9 and the image plane 10 of the observation apparatus of the present invention is shorter than that of the conventional observation apparatus by "L". Thereby, the length in the direction of the optical axis of the photographing means 5 becomes shorter than that of the conventional observation apparatus. As the result, the observation apparatus 1 becomes compact.

Accordingly, it becomes easier to move the whole photographing means 5 (hereinafter referred to as a "full-floating").

Furthermore, since the total length of the photographing means can be short without shortening the focal length of the object compound lens 8 and the focal length of the image compound lens 9 (without making lens power higher), fading of an image due to out of focus is reduced. It is preferable for the photographing means.

According to the present invention, full-floating can be performed as mentioned hereinbefore, the image ray transmitted from the object compound lens 8 to the image compound lens 9 is not required to be collimated exactly. Therefore, the photographing means 5 can be provided with the focusing system even in the side of the image compound lens 9 thereof.

In such an apparatus for observation at low magnification (e.g. observation of a retinal vessel), the length in the direction of the optical axis is not long. There is no need for the image compound lens to employ such a construction that the convex compound lens is alienated from the concave compound lens. The image compound lens can employ such a construction as to consist of only the convex compound lens.

The focusing system is not limited to be specific one. It may be employed such a system that the convex compound lens 11 is moved by a miniature motor 13 with a reducer and at the same time rotating angle of the motor 13 is detected by an encoder 14 connected with the miniature motor 13.

The illumination optics 7 is fixed to the frame 1a of the main body. The illumination optics has such a construction that a light source for observation 15 is adjacent to a condensing lens 16, the condensing lens 16 is adjacent to a lens stop 17, and the lens stop 17 is adjacent to a collimating lens 18, and the collimating lens 18 is adjacent to a refleting mirror 19. The above-mentioned reflecting mirror 19 is arranged between the object compound lens 8 and the image compound lens 9 in the photographic optics 2. As a result, the photographic optics 2 and the illumination optics 7 share the object compound lens 8.

Furthermore, the frame 1a of the main body is provided with a biasing means 20 for constantly biasing the movable photographing means 5 along with the optical axis thereof in such a manner that a tip portion of the object compound lens 8 is coming into contact with an eye, which is an object of inspection. By virtue of the biasing means 20, out of focus does not happen since the tip portion of the object compound lens 8 can move constantly and follow even if a face of a patient moves or location of a cornea moves due to a change of intraocular pressure or pulse pressure.

Figure 4:
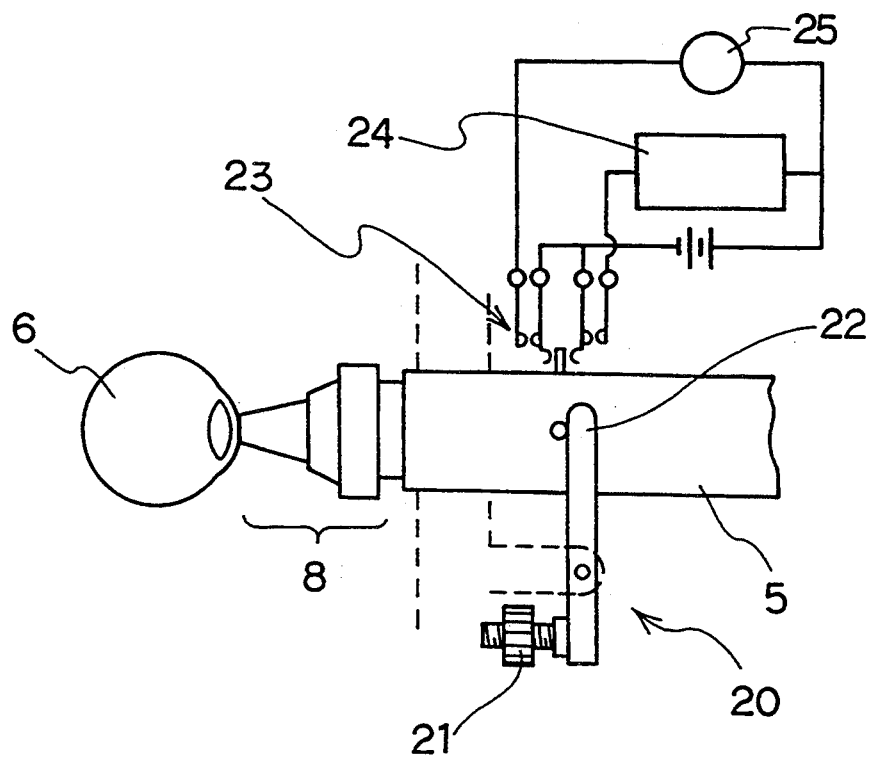
FIG. 4 an illustrating is view showing an embodiment of biasing device used in the eye observation apparatus of the present invention.

As the biasing means 20, such a normal means that the eye 6 is constantly contacted with the tip portion of the object compound lens 8 by weak and constant force can be used. For instance, there is such a biasing means (with reference to FIG. 4) disclosed in Japanese Examined Patent Publication No. 36969/1983 that a lever 22 will experience moments imposed by an adjustable weight 21, thereby the tip portion of the object compound lens 8 is coming into contact with the eye 6, when the eye 6 is pushed excessively by the tip portion of the object compound lens 8, a switch 23 operates and a buzzar 24 whistles, and when the eye 6 is parted from the object compound lens 8 excessively, a lamp 25 lights.

As a biasing means, there is such a biasing means (not shown in Figure) disclosed in Japanese Unexamined Patent Publication No. 142007/1983 or Japanese Unexamined Patent Publication No. 39703/1989 that the eve 6 is contacted with the tip portion of the object compound lens 8 by means of an extension spring.

Figure 5:
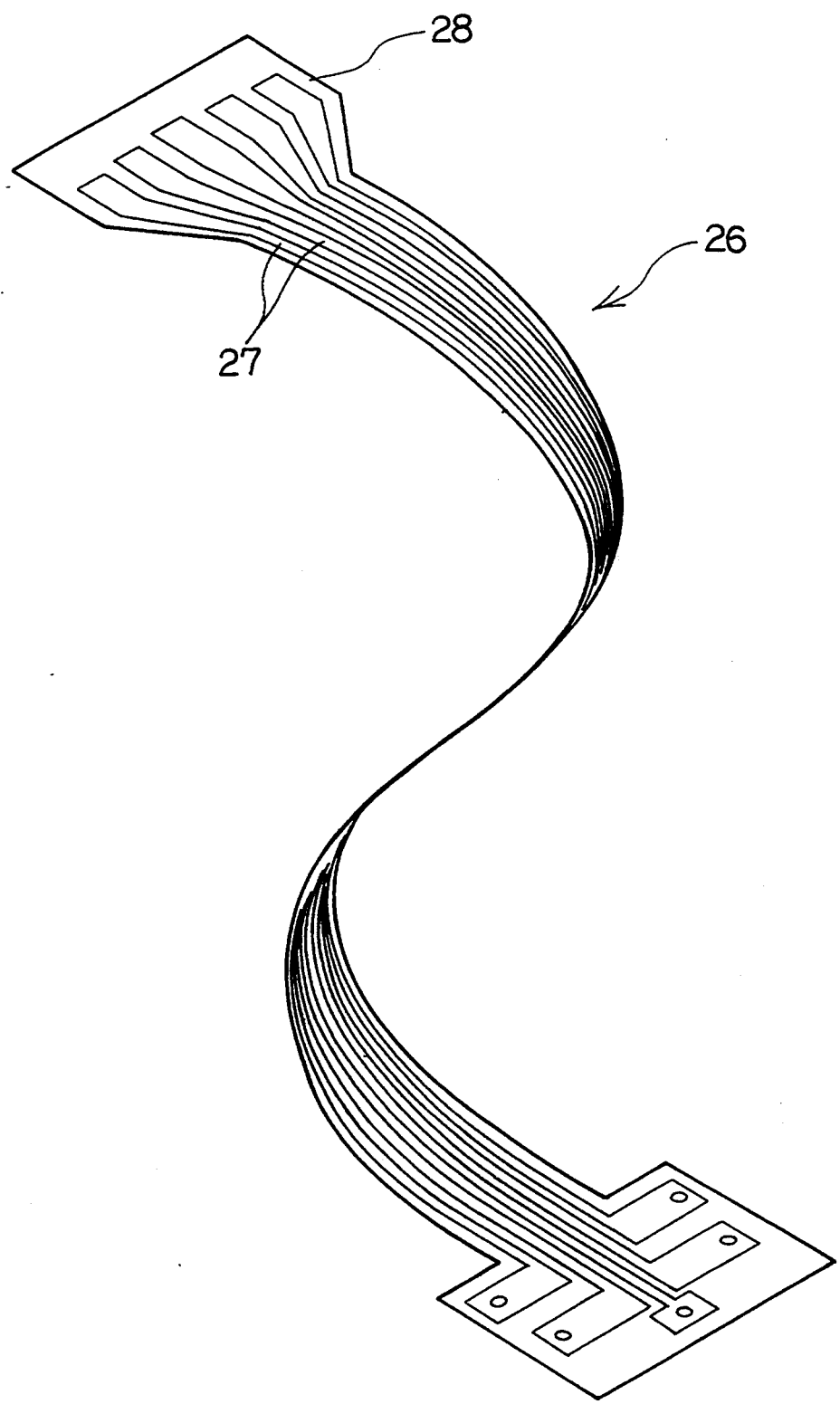
FIG. 5 is a perspective view showing a flexible electrical cable in FIG. 1.
Figure 6:
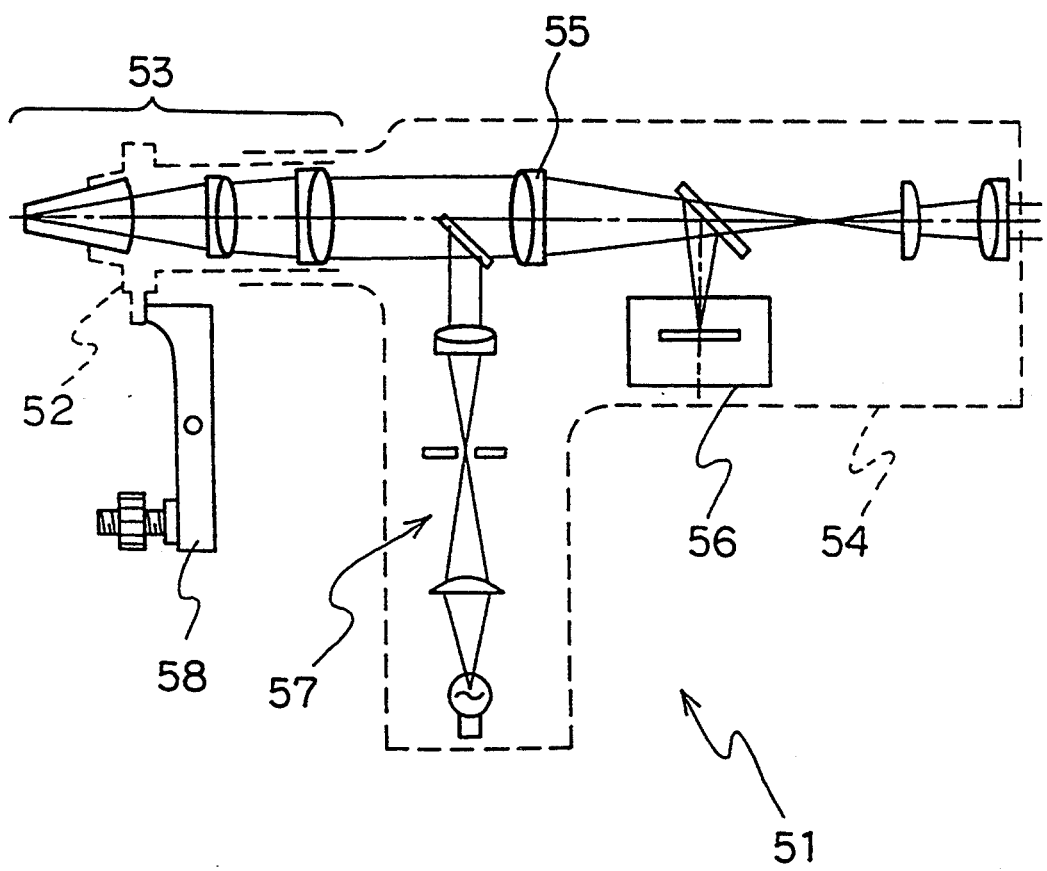
FIG. 6 is an optical-path diagram showing an embodiment of conventional eye observation apparatus.
Figure 7:
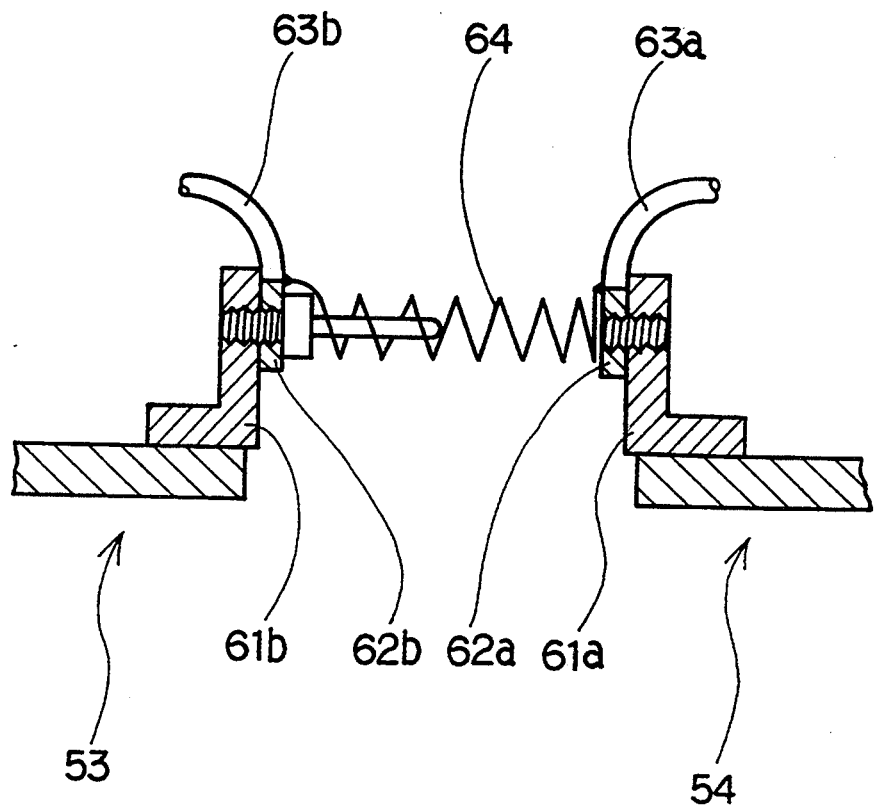
FIG. 7 is a front view showing an example of wiring for electric connection.

In the eye observation apparatus of the embodiment, a flexible electrical cable 26 (flexible flat cable "FFC" or flexible print circuit "FPC") which connects the frame 1a with the photographing means 5 is employed as a cable for supplying electric power with the focusing system, the biasing means 20 or a CCD image is sensor in the camera 26. The flexible electrical cable well-known. For example, as shown in FIG. 5, there is the flexible electrical cable wherein plurality of tinned phosphor bronze foil wires are coated in such a manner as to be sandwitches by polyvinyl chloride films.

The cable wherein film, such as polyvinyl chloride, is onesidedly adhered to the tinned phosphor bronze foil wires can the be used. Furthermore, the cable wherein wire poriton is formed by deposition or printing, can also be used. These flexible electrical cable has such advantages that wiring plural systems collectively can be performed, wiring even in narrow space can be performed and connection with machinary is easy. The flexible electrical cable can he also used in such a case that required number of cable is few.

Moreover, in the embodiment, the flexible electrical cable was employed in order to reduce reaction force generated by bending the cable when the tip portion of the object compound lens 8 is coming into contact with eye 6 in consideration of good flexiblity of the cable. That is to say, the reaction force generated by bending the flexible electrical cable hardly comes out when the tip portion of the object compound lens 8 is forced to contact with with a proper pushing force by moving the object compound lens 8. Therefore, the eye is not badly affected by the object compound lens 8.

Next, the operation and using method of the observation apparatus 1 of the embodiment constructed as mentioned hereinbefore is explained.

Firstly, illuminating ray emitted from a light source for observation 15 of the illumination optics is transmitted through the condensing lens 16, the lens stop 17 and collimating lens 18 so that illuminating ray becomes collimated ray, then collimated ray is transmitted through the object compound lens 8 by reflected by the reflection mirror 19, and illuminates the inspection portion.

Next, the image ray emitted from the inspection portion of the eye 6 is collimated to some extent by the object compound lens 8 and imaged on the image plane 10 by image compound lens 9. That is to say, the convex compound lens 11 has the focusing function and the object compound lens 8 does not have the focusing function. Therefore, the above-mentioned ray emitted from any part of the eye is not perfectly collimated ray. However, there is no problem since the focus can be checked by moving the convex compound lens 11 along with the optical axis. Further, if the focus is once checked, out of focus does not happen since the whole photographing means 5 including the image plane 10 moves.

In the embodiment, the observation apparatus 1 has such a focusing system that the convex compound lens 11 of the image compound lens 9 can be moved.

According to the present invention, the focusing system is not limited to the embodiment. There can be such a focusing system that the concave compound lens 12 can be moved or a part of the object compound lens 8 can be moved. The image plane 10 can be provided with the focusing system.

When the image of the inspection portion is enlarged with a high magnification in such a case as to observe endothelium cornea or corneal epithelium, length in the direction of optical axis of the observation apparatus becomes long. On the contrary, as mentioned embodiment, the image compound lens 9 which has such a construction that the convex compound lens 11 is alienated from the concave compound lens 12 can sharply shorten the distance between the image compound lens 9 and the image plane 10 compared with the image compound lens which is composed of only the convex compound lens 11. As a result, it is easy that the photographing means 5 can be moved along with the optical axis thereof, i.e. full-floating can be easily performed as mentioned hereinbefore.

Moreover, the observation apparatus can be conveniently handled since the whole observation apparatus is compact.

The observation apparatus of the present invention is not required to position the optical axis. Therefore, it is easy to assemble the apparatus and the location of setting the focusing system can be designed more freely than the conventional observation apparatus.

Though several embodiments of the invention are described above, it is to be understood that the present invention is not limited to the above-mentioned embodiments, and various changes and modifications may be made in the invention without departing from the sprit and scope thereof.

What we claimed is:

1. Eye observation apparatus, comprising:
   illumination optics which is fixed on a frame of a main body, said illumination optics illuminating a portion for inspection;
   a photographing means movably mounted within said frame of the main body along with an optical axis; and
   a biasing means for biasing said photographing means so that a tip portion of said photographing means comes into slight contact with an eye, wherein said photographing means includes an eye piece and a camera having an image plane which is emitted from said portion for inspection to reach said image plane, said photographic optics having an object compound lens and an image compound lens,
   wherein said photographic means has object compound lens and image compound lens having convex compound lens and concave compound lens,
   wherein said convex compound lens located in a side of said object compound lens and alienated from said concave compound lens in a side of said image plane, and wherein one of said convex compound lens and said concave compound lens is movable on the optical axis.

2. Eye observation apparatus of claim 1, wherein said photopraphing means has an electrical equipment and a flexible electrical cable for electrical connection is equipped between said photopraphing means and said frame of the main body.

3. Eye observation apparatus of claim 2, wherein said flexible electrical cable comprises plurality of foils having electric conductivity and a synthetic resin film, said synthetic resin film being onesidedly attached to said plurality of foils.

* * * * *